(12) United States Patent
Bache et al.

(10) Patent No.: US 10,813,384 B2
(45) Date of Patent: Oct. 27, 2020

(54) ELECTRONIC VAPING DEVICE HAVING FORMULATION LEVEL INDICATOR

(71) Applicant: Altria Client Services LLC, Richmond, VA (US)

(72) Inventors: Terrance Theodore Bache, Richmond, VA (US); Christopher S. Tucker, Midlothian, VA (US); Raymond W. Lau, Richmond, VA (US)

(73) Assignee: Altria Client Services LLC, Richmond, VA (US)

( * ) Notice: Subject to any disclaimer, the term of this patent is extended or adjusted under 35 U.S.C. 154(b) by 23 days.

(21) Appl. No.: 15/858,625

(22) Filed: Dec. 29, 2017

(65) Prior Publication Data
US 2019/0200675 A1   Jul. 4, 2019

(51) Int. Cl.
| | |
|---|---|
| *A24F 47/00* | (2020.01) |
| *A61M 15/06* | (2006.01) |
| *A61M 11/04* | (2006.01) |
| *G08B 5/36* | (2006.01) |
| *G09F 13/04* | (2006.01) |
| *G09F 13/22* | (2006.01) |
| *H05B 3/44* | (2006.01) |

(52) U.S. Cl.
CPC ......... *A24F 47/008* (2013.01); *A61M 11/042* (2014.02); *A61M 15/06* (2013.01); *G08B 5/36* (2013.01); *G09F 13/04* (2013.01); *G09F 13/22* (2013.01); *H05B 3/44* (2013.01); *G09F 2013/222* (2013.01)

(58) Field of Classification Search
None
See application file for complete search history.

(56) References Cited

U.S. PATENT DOCUMENTS

| | | | |
|---|---|---|---|
| 6,880,396 | B2 | 4/2005 | Rait |
| 6,978,984 | B2 | 12/2005 | Kang |

(Continued)

FOREIGN PATENT DOCUMENTS

| | | |
|---|---|---|
| CN | 204104842 U | 1/2015 |
| EP | 3180997 A1 | 6/2017 |

(Continued)

OTHER PUBLICATIONS

International Search Report and Written Opinion for corresponding PCT Application No. PCT/EP2018/085669 dated Apr. 15, 2019.

(Continued)

*Primary Examiner* — Thor S Campbell
(74) *Attorney, Agent, or Firm* — Harness, Dickey & Pierce, P.L.C.

(57) ABSTRACT

The e-vaping device includes a vaporizer assembly, which includes a heating element, a pre-vapor formulation reservoir, a pre-vapor formulation level indicator including a plurality of discrete indicator segments, and at least one processor. The pre-vapor formulation reservoir may be configured to contain a pre-vapor formulation and the at least one processor may be configured to determine a difference between a first duty cycle of power supplied to the heating element and a second duty cycle of power supplied to the heating element; and adjust the indicator based on the determined duty cycle difference.

23 Claims, 11 Drawing Sheets

(56) References Cited

U.S. PATENT DOCUMENTS

| | | |
|---|---|---|
| 7,009,519 B2 | 3/2006 | Leonard et al. |
| 7,307,779 B1 | 12/2007 | Cernasov |
| 7,581,442 B1 | 9/2009 | Dietz et al. |
| 8,343,436 B2 | 1/2013 | Laukhina et al. |
| 8,467,981 B2 | 6/2013 | Mukherjee et al. |
| 8,621,224 B2 | 12/2013 | Jung et al. |
| 8,634,127 B2 | 1/2014 | Shih et al. |
| 8,641,617 B2 | 2/2014 | Natarajan |
| 8,910,640 B2 | 12/2014 | Sears et al. |
| 9,326,547 B2 | 5/2016 | Tucker et al. |
| 9,510,623 B2 | 12/2016 | Tucker et al. |
| 2006/0144140 A1 | 7/2006 | Hache |
| 2007/0069883 A1 | 3/2007 | Collier et al. |
| 2011/0295095 A1 | 12/2011 | Deppert et al. |
| 2012/0019495 A1 | 1/2012 | Chang et al. |
| 2013/0192619 A1 | 8/2013 | Tucker et al. |
| 2013/0192623 A1 | 8/2013 | Tucker et al. |
| 2013/0302627 A1 | 11/2013 | Roehrig et al. |
| 2013/0319439 A1 | 12/2013 | Gorelick et al. |
| 2014/0096782 A1* | 4/2014 | Ampolini .......... A24F 47/008 131/328 |
| 2014/0230835 A1 | 8/2014 | Saliman |
| 2014/0261486 A1 | 9/2014 | Potter et al. |
| 2014/0270727 A1 | 9/2014 | Ampolini et al. |
| 2014/0345633 A1* | 11/2014 | Talon .......... A61M 11/042 131/329 |
| 2015/0020823 A1 | 1/2015 | Lipowicz et al. |
| 2015/0020825 A1 | 1/2015 | Galloway et al. |
| 2015/0053217 A1 | 2/2015 | Steingraber et al. |
| 2015/0082882 A1 | 3/2015 | Antocci |
| 2015/0128976 A1 | 5/2015 | Verleur et al. |
| 2015/0136158 A1 | 5/2015 | Stevens et al. |
| 2015/0208731 A1 | 7/2015 | Malamud et al. |
| 2015/0313275 A1 | 11/2015 | Anderson et al. |
| 2015/0335074 A1* | 11/2015 | Leung .......... A61M 11/044 131/328 |
| 2016/0029977 A1 | 2/2016 | Di Resta et al. |
| 2016/0089508 A1 | 3/2016 | Smith et al. |
| 2016/0091194 A1 | 3/2016 | Liu |
| 2016/0374397 A1* | 12/2016 | Jordan .......... A24F 47/008 131/329 |
| 2019/0200675 A1* | 7/2019 | Bache .......... A24F 47/008 |

FOREIGN PATENT DOCUMENTS

| | | |
|---|---|---|
| EP | 3400815 A1 | 11/2018 |
| WO | WO-2004/049237 | 8/2004 |
| WO | WO-2015/026948 A1 | 2/2015 |
| WO | WO-2015035510 | 3/2015 |
| WO | WO-2015/063126 A1 | 5/2015 |
| WO | WO-2015/179641 A1 | 11/2015 |
| WO | WO-2016/210242 A1 | 12/2016 |
| WO | WO-2017/055795 A1 | 4/2017 |
| WO | WO-2017/141358 A1 | 8/2017 |

OTHER PUBLICATIONS

Written Opinion of the International Preliminary Examining Authority dated Dec. 12, 2019 in PCT Application No. PCT/EP2018/085669.

International Preliminary Report on Patentability dated May 26, 2020 in PCT Application No. PCT/EP2018/085669.

* cited by examiner

ELECTRONIC VAPING DEVICE HAVING FORMULATION LEVEL INDICATOR

BACKGROUND

Field

One or more example embodiments relate to electronic vaping devices.

Description of Related Art

An electronic vaping (e-vaping) device includes a heating element, which vaporizes a pre-vapor formulation to produce a vapor to be drawn through outlets of the e-vaping device. Electronic vaping devices may be referred to as e-vapor devices or e-vaping devices.

An e-vaping device further includes a power supply, such as a battery, arranged in the e-vaping device. The battery is electrically connected to the heating element to power the heating element, such that the heating element heats to a temperature sufficient to convert the pre-vapor formulation to a vapor. The vapor exits the e-vaping device through a mouth-end piece including at least one outlet.

SUMMARY

This section provides a general summary of the disclosure, and is not a comprehensive disclosure of its full scope or all of its features.

At least one example embodiment relates to an e-vaping device.

The e-vaping device includes a vaporizer assembly (also referred to as a vaporizer section or cartridge), which includes a heating element, a pre-vapor formulation reservoir, a pre-vapor formulation level indicator including a plurality of discrete segments, and at least one processor. The pre-vapor formulation reservoir may be configured to contain a pre-vapor formulation and the at least one processor may be configured to determine a difference between a first duty cycle of power supplied to the heating element and a second duty cycle of power supplied to the heating element and adjust the indicator based on the determined duty cycle difference.

Further areas of applicability will become apparent from the description provided herein. The description and specific examples in this summary are intended for purposes of illustration only and are not intended to limit the scope of the present disclosure.

BRIEF DESCRIPTION OF THE DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Figure 1:
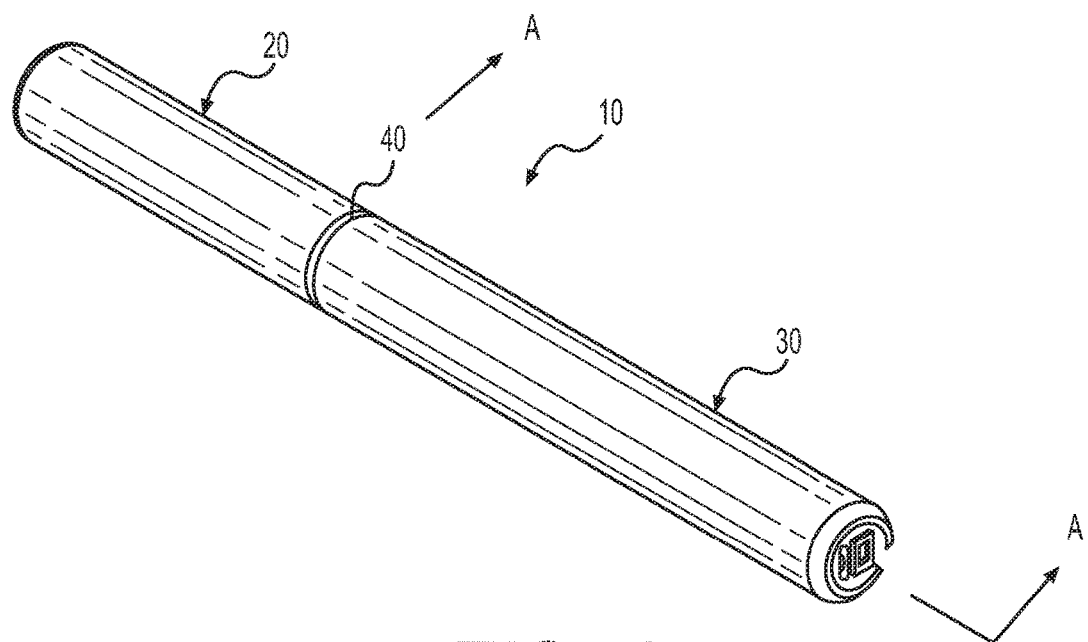
FIG. 1 illustrates an example embodiment of an electronic vaping device.

Example embodiments will now be described more fully with reference to the accompanying drawings.

Example embodiments are provided so that this disclosure be thorough, and will fully convey the scope to those who are skilled in the art. Numerous specific details are set forth such as examples of specific items, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or items, but do not preclude the presence or addition of one or more other features, integers, steps, operations, elements, items, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," or the like). As used herein, the term "and/or" includes any and all combinations of one or more of the associated listed items.

Although the terms first, second, third, or the like may be used herein to describe various elements, items, regions, layers and/or sections, these elements, items, regions, layers and/or sections should not be limited by these terms. These terms may be only used to distinguish one element, item, region, layer or section from another region, layer or section. Terms such as "first," "second," and other numerical terms when used herein do not imply a sequence or order unless clearly indicated by the context. Thus, a first element, item, region, layer or section discussed below could be termed a second element, item, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

A pre-vapor formulation is a material or combination of materials that may be transformed into a vapor. For example, the pre-vapor formulation may be a liquid, solid, and/or gel formulation including, but not limited to: water, beads, solvents, active ingredients, ethanol, plant extracts, natural or artificial flavors, and/or vapor formers such as glycerin and propylene glycol. U.S. patent application Ser. No. 14/602,099 (Publication No. 2015/0313275), U.S. patent application Ser. No. 14/333,212 (Publication No. 2015/0020823) and U.S. patent application Ser. No. 13/756,127 (Publication No. 2013/0192623), which are incorporated herein by reference in their entirety, disclose examples of formulation mixtures.

The pre-vapor formulation may include nicotine or may exclude nicotine. The pre-vapor formulation may include one or more tobacco flavors. The pre-vapor formulation may include one or more flavors that are separate from one or more tobacco flavors.

In some example embodiments, a pre-vapor formulation that includes nicotine may also include one or more acids. The one or more acids may be one or more of pyruvic acid, formic acid, oxalic acid, glycolic acid, acetic acid, isovaleric acid, valeric acid, propionic acid, octanoic acid, lactic acid, levulinic acid, sorbic acid, malic acid, tartaric acid, succinic acid, citric acid, benzoic acid, oleic acid, aconitic acid, butyric acid, cinnamic acid, decanoic acid, 3,7-dimethyl-6-octenoic acid, 1-glutamic acid, heptanoic acid, hexanoic acid, 3-hexenoic acid, trans-2-hexenoic acid, isobutyric acid, lauric acid, 2-methylbutyric acid, 2-methylvaleric acid, myristic acid, nonanoic acid, palmitic acid, 4-penenoic acid, phenylacetic acid, 3-phenylpropionic acid, hydrochloric acid, phosphoric acid, sulfuric acid and combinations thereof.

The pre-vapor formulation may also or instead be a pre-dispersion formulation in which the formulation may or may not be vaporized but may also or instead be dispersed.

FIG. 1 illustrates an example embodiment of an electronic vaping e-vaping) device 10.

FIG. 1 is an illustration of an assembled electronic vaping (e-vaping) device 10, in accordance with an example embodiment. The device 10 may include two major sections: a cartridge 20 and a power section 30. Alternatively, the device 10 may include more than two sections, or the device 10 may be one integrated section. The power section 30 may be reusable, or alternatively the power section 30 may be disposable. The cartridge 20 may be disposable, or alternatively the cartridge 20 may be reusable. The sections 20/30 may be connected to each other via threaded connections (not shown). Alternatively, the sections 20/30 may be connected to each other via other structures such as a snug-fit connection, a detent, a pressure-fitting, a clamp and/or a clasp, or the like. The cartridge 20 is configured to heat a pre-vapor formulation to generate a vapor.

Figure 2:
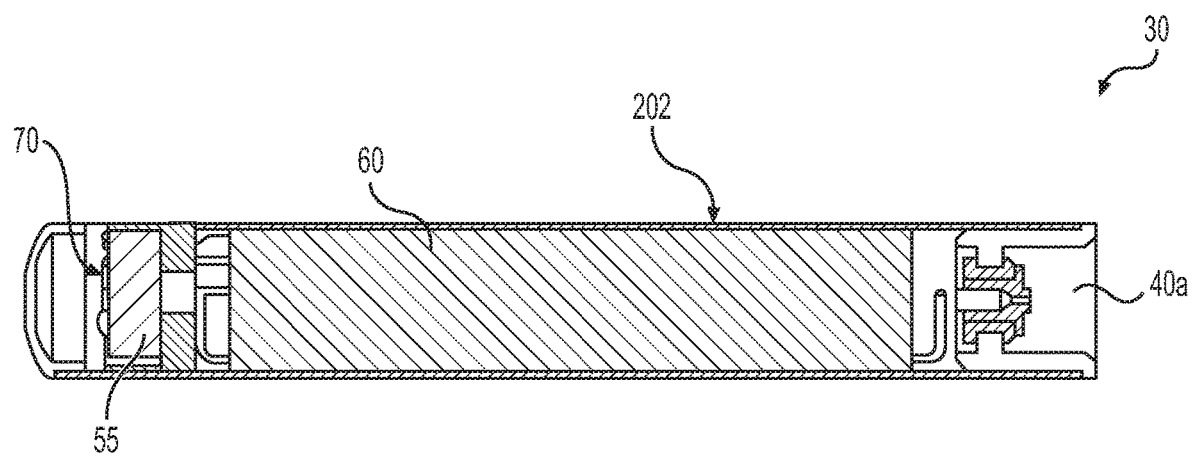
FIG. 2 illustrates cross-sectional view of a power section of the example electronic vaping device.

FIG. 2 is an illustration of a cross-sectional view of a power section 30 of the e-vaping device 10 of FIG. 1 (i.e., cross-sectional view 'A-A' of FIG. 1), in accordance with an example embodiment. The power section 30 provides power to the cartridge 20. As mentioned above, the power section 30 may be a reusable section of an e-vaping device. In this case, the reusable section may be capable of being recharged by an external charging device. Alternatively, the power section 30 may be a disposable section of an e-vaping device, such that the power section 30 may be used only until the energy from a power supply 60 (described below) is depleted.

The power section 30 is not limited to a battery as a power supply; it may be any other power supply. The power supply 60 may be a Lithium-ion battery or one of its variants, for example, a Lithium-ion polymer battery, Lithium-iron-phosphate, or the like. Alternatively, the power supply may be a nickel-metal hydride battery, a nickel cadmium battery, a lithium-manganese battery, a lithium-cobalt battery or a fuel cell. The e-vaping device may be operable by an adult vaper until the energy in the power supply is depleted or in the case of lithium polymer battery, a minimum voltage cut-off level is achieved.

With further reference to FIG. 2, the power section 30 includes a first connector part 40a, a pressure sensor 55, a power supply 60 and a controller 70 within a housing shell 202. The housing shell 202 may be formed of plastic and may optionally include a metal (e.g., aluminum) coating, although other suitable materials may be used. The controller 70 may be a processor, a microprocessor, a controller, an application specific integrated circuit (ASIC), or other such hardware.

The controller 70 may connect to the pressure sensor 55, which is operable to sense an air pressure drop within the e-vaping device and initiate application of voltage from the power section 30 to a heating element in the cartridge 20 when the cartridge 20 is connected to the power section 30.

When the power section 30 is connected to the cartridge 20, the power supply 60 is electrically connected with the heating element of the cartridge 20 upon sensing negative pressure within the cartridge 20 and/or the power section 30 applied by an adult vaper by the pressure sensor 55. Air is drawn primarily into a central air passage of the cartridge through a mouth-end piece of the e-vaping device 10. Example embodiments are not limited to e-vaping devices using a pressure sensor to activate the vaping. Rather, example embodiments are also applicable to e-vaping devices that maybe activated in other ways, such as via a push button, a capacitive button, or the like.

The first connector part 40a may be a female connector capable of connecting to a male connector on another e-vaping element, such as the cartridge 20 of the e-vaping device 10 (see FIGS. 3 and 4A-4C). Alternatively, the first connector part 40a may be a male connector capable of connecting to a female connector on another section of an e-vaping device. A second connector part 40b may be a male connector capable of connecting to a female connector on another e-vaping element, such as the power section 30 of the e-vaping device 10 (see FIGS. 3 and 4A-4C). Alternatively, the second connector part 40b may be a female connector capable of connecting to a male connector on another section of an e-vaping device. Distal ends of the connectors 40a/40b may define threads (not shown) that may be capable of mating with threads (not shown) on another e-vaping section.

Figure 3:
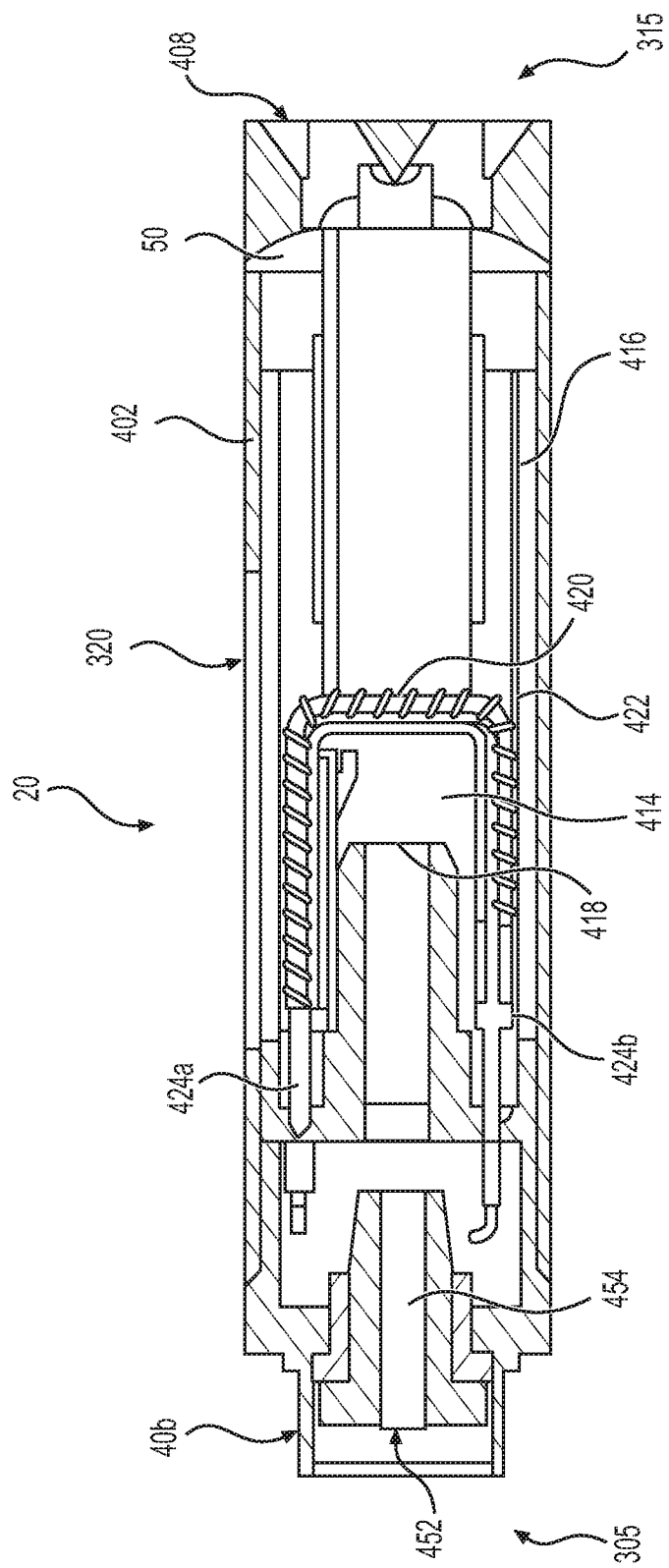
FIG. 3 illustrates a cross-sectional view of an example embodiment of a cartridge of an electronic vaping device.

FIG. 3 is a cross-sectional view of an example embodiment of the cartridge 20 of the e-vaping device 10. As with the power section 30, different cartridges or sections can be employed with the present subject matter.

Referring to FIG. 3, the cartridge 20 includes the housing 402 an indicator 320, with a mouth-end 315 and a connector end 305. The housing 402 may be formed of metal (e.g., stainless steel), although other suitable materials may be used.

The cartridge 20 heats a pre-vapor formulation contained within the cartridge 20 to generate a vapor capable of being drawn through a multi-port insert 50 in the mouth-end 315. U.S. patent application Ser. No. 13/741,254 (Publication No. 2013/0192619), which is incorporated herein by reference in its entirely, discloses an example dispersion multi-port mouth insert.

The cartridge 20 includes an inner tube 414, a pre-vapor formulation reservoir 416 for storing or containing a pre-vapor formulation, and a cartridge inlet 418. The inner tube 414 defines a passage that is generally coaxially positioned in and with the housing 402. The pre-vapor formulation reservoir 416 may be contained in an outer annulus between the housing 402 and the inner tube 414.

In at least one example embodiment, the reservoir 416 contains the pre-vapor formulation and, optionally, a storage medium (e.g., fibrous medium) configured to disperse and/or regulate a flow of the pre-vapor formulation in the reservoir. For example, the storage medium may be a wrapping of gauze about the inner tube. The storage medium comprises an outer wrapping of gauze surrounding an inner wrapping of gauze of the same or different material. In at least one example embodiment, the storage medium of the reservoir 416 is constructed from an alumina ceramic in the form of loose particles, loose fibers, or woven or nonwoven fibers, or alternatively the storage medium is constructed from a cellulosic material such as cotton or gauze material or polymer material, such as polyethylene terephthalate in the form of a bundle of loose fibers.

The fibers of the storage medium may have a diameter ranging in size from about 6 microns to about 15 microns (e.g., about 8 microns to about 12 microns or about 9 microns to about 11 microns). The storage medium may be a sintered, porous or foamed material. Also, the fibers may be sized to be irrespirable and may have a cross-section that has a Y-shape, cross shape, clover shape or any other suitable shape. In some example embodiments, the pre-vapor formulation reservoir 416 may include a filled tank lacking any storage medium and containing only pre-vapor formulation.

The mouth-end 315 includes the multi-port insert 50, which may include outlets 408 that are in fluid communication with the inner tube 414, which extends to an anode 452 of the second connector part 40b. The anode 452 may include a through-hole 454, which is in fluid communication with the inner tube 414 on one end and in fluid communication with air inlets (not shown) on an opposing end.

In at least some example embodiments, the cartridge 20 may further include a heating element 420, a wick 422, and electrode leads 424a and 424b, which are provided to electrically couple the heating element 420 (alternatively referred to as "heater") to a power supply when the cartridge 20 is connected to a power supply section such as power section 30.

When the cartridge 20 is connected to the power section 30, the power supply 60 may be operably connected to the heating element 420 to apply a voltage across the heating element 420. Furthermore, the power supply 60 supplies power to a controller on a printed circuit board 72, as will be described in greater detail.

Figure 4A:
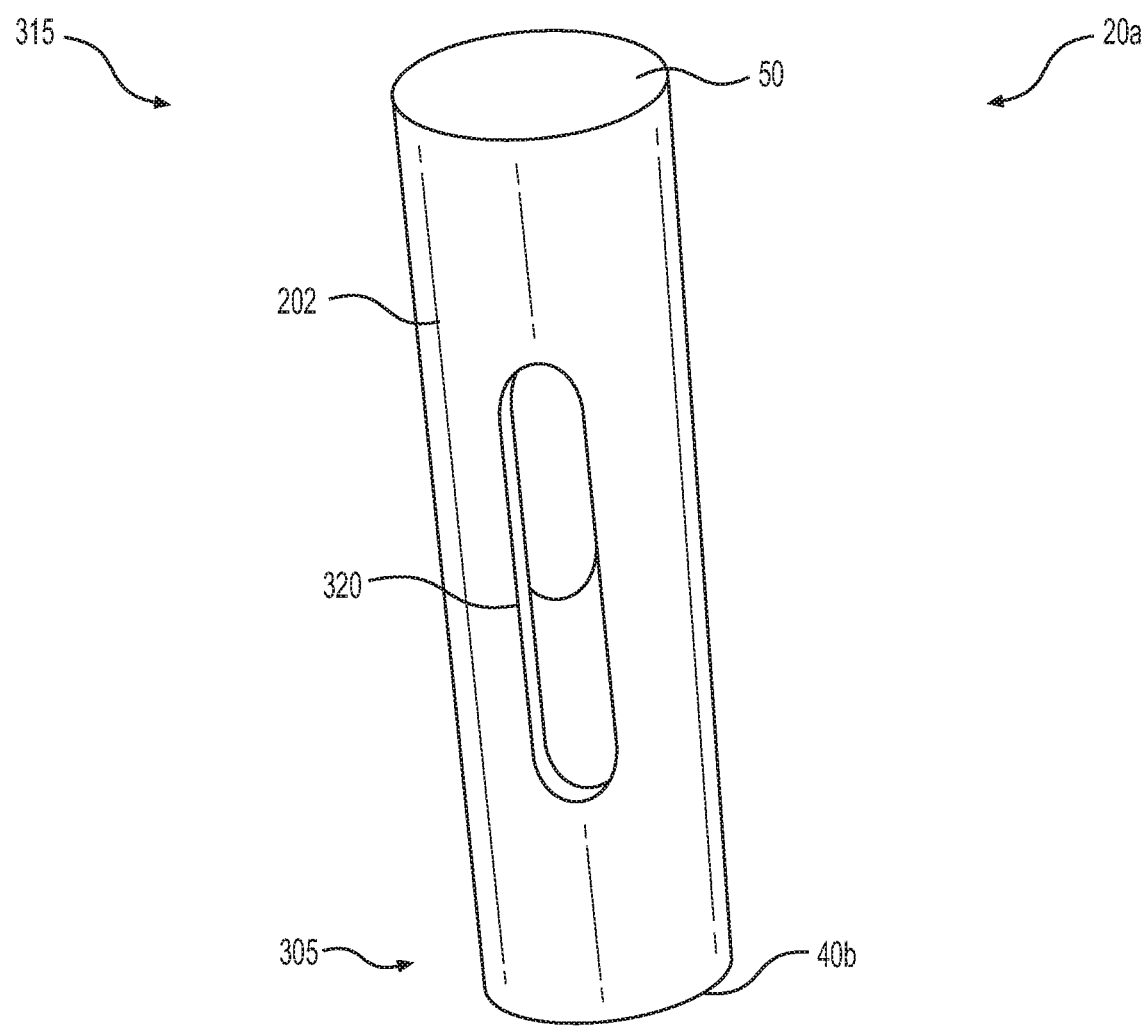
FIG. 4A illustrates an example embodiment of a cartridge of an electronic vaping device.
Figure 4B:
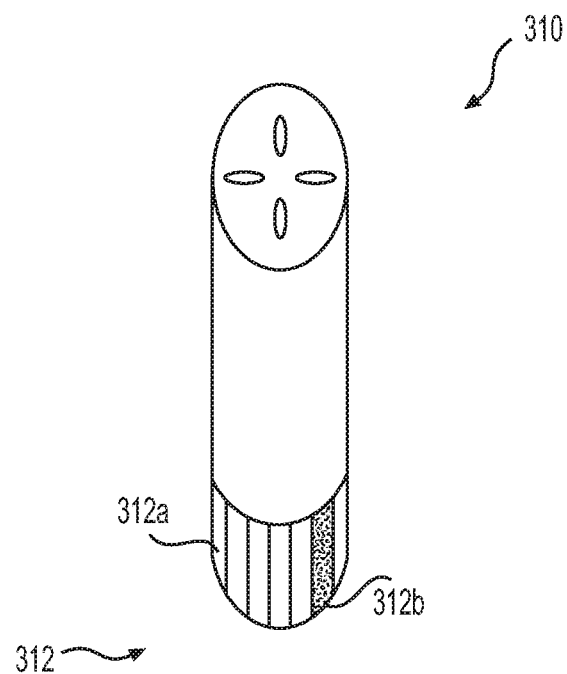
FIG. 4B illustrates another example embodiment of a cartridge of an electronic vaping device.
Figure 4C:
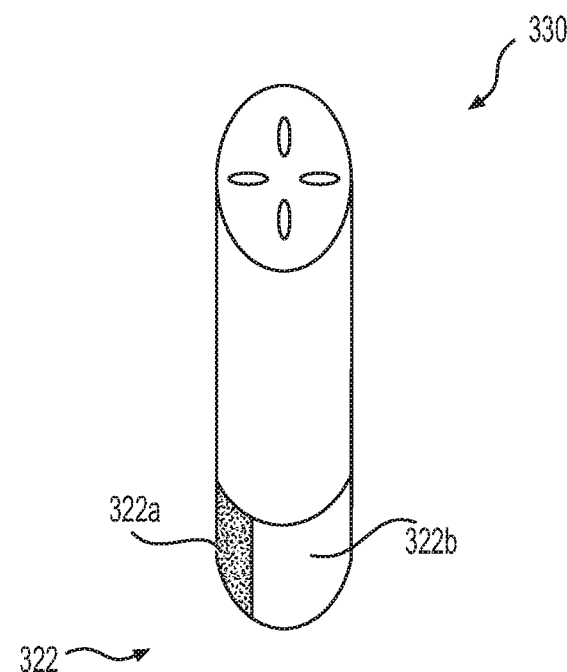
FIG. 4C illustrates another example embodiment of a cartridge of an electronic vaping device.

FIGS. 4A-4C illustrate example embodiments of cartridges. Referring to FIG. 4A, the cartridge 20a includes the indicator 320 for displaying an amount of fluid remaining in the reservoir 416 of the cartridge 20. The displayed amount may be analogous to the amount of fluid remaining in the reservoir 416. In one example, a fully powered indicator 320 may represent a completely full reservoir. Alternatively, a fully powered indicator 320 may represent a completely depleted reservoir. For example, in a configuration of the example embodiment, if the pre-vapor formulation in the cartridge 20 is depleted, the indicator 320 may be configured to be fully powered. In another configuration of the example embodiment, if the cartridge 20a is full of pre-vapor formulation, the indicator 320 may be configured to be fully powered. In another configuration of the example embodiment, if the cartridge 20a is partially full, the indicator 320 may be configured to be partially powered. The controller 70 controls power delivered to the indicator 320 according to an amount of pre-vapor formulation in the reservoir.

In FIG. 4A, the cartridge 20a is shown having the multi-port insert 50 at a mouth-end 315, the second connector part 40b at a connector end 305 and a housing 402. The indicator 320 is longitudinally arranged on a surface of the cartridge 20a. The indicator 320 may have an elongate shape and extend longitudinally along a lengthwise axis of the cartridge 20a. In the example, the indicator 320 is shown as a single display; however, embodiments should not be limited to this example. The indicator 320 may be configured to display an analogous representation of an amount of fluid remaining in the cartridge 20a. Also, the indicator 320 may include a plurality of discrete indicators, each of which may be configured to receive power independent of the other discrete indicators. The amount of discrete indicators receiving power may be analogous to the amount of pre-vapor formulation remaining in the cartridge 20a.

FIG. 4B shows another example embodiment of a cartridge.

Referring to FIG. 4B, the cartridge 310 is similar to the cartridge 20a, except that the cartridge 310 includes an indicator 312 at an end thereof. The indicator 312 may encircle the entire circumference of the cartridge 310, partially encircle the circumference of the cartridge 310, or intermittently encircle the circumference of the cartridge 310. According to at least one example embodiment, the indicator 312 is configured to display a plurality of discrete segments 312a of the indicator 312, wherein the discrete segments 312a are configured to each independently receive voltage from the power section 30 when the cartridge 310 is connected to the power section 30. Each of the discrete segments 312a may be powered simultaneously with, but independent from, the remainder of the discrete segments. For example, the discrete segment 312a is illustrated as receiving power and a second discrete segment 312b is illustrated as being without power. Discrete segments are discussed in more detail below.

Various methods may be used to determine an order in which the discrete segments may be powered and will not be discussed in detail herein. The indicator 312 is configured to provide an indication of how much pre-vapor formulation remains in the reservoir of the cartridge. Operation of the indicator will be discussed in detail below.

Referring to FIG. 4C, the cartridge 330 is similar to the cartridge 20a, except that the cartridge 330 includes an indicator 322. The indicator 322 may be monolithic and may include charged material 322a and uncharged material 322b.

The indicator 322 is configured to provide an analogous representation of an amount of pre-vapor formulation remaining in the cartridge 330. The indicator 322 may be and is not limited to electronic paper ("E-paper"), an Organic Light Emitting Diode ("OLED"), a Light Emitting Diode, or the like. The indicator 322 may have a singular construction that can be configured to indicate an analogous representation of the pre-vapor formulation remaining in the reservoir. Alternatively, or additionally, the indicator 322 may be a plurality of separated discrete indicator segments 322a and 322b. In the case of a plurality of discrete indicator segments the number of powered discrete segments reflects the amount of pre-vapor formulation in the cartridge.

The indicator segments 322a, 322b may be arranged in a column longitudinally along the cartridge, columns of dot-, dash-, or other-shaped lights arranged in rows circumferentially along the cartridge, or the like. The shape of the indicator segment, plurality of rings, differently shaped distinct objects such as squares, circles, ovals, flowers, stars, trapezoids, rectangles, or the like. Operation of the indicator 322 is discussed in more detail below.

Figure 5:
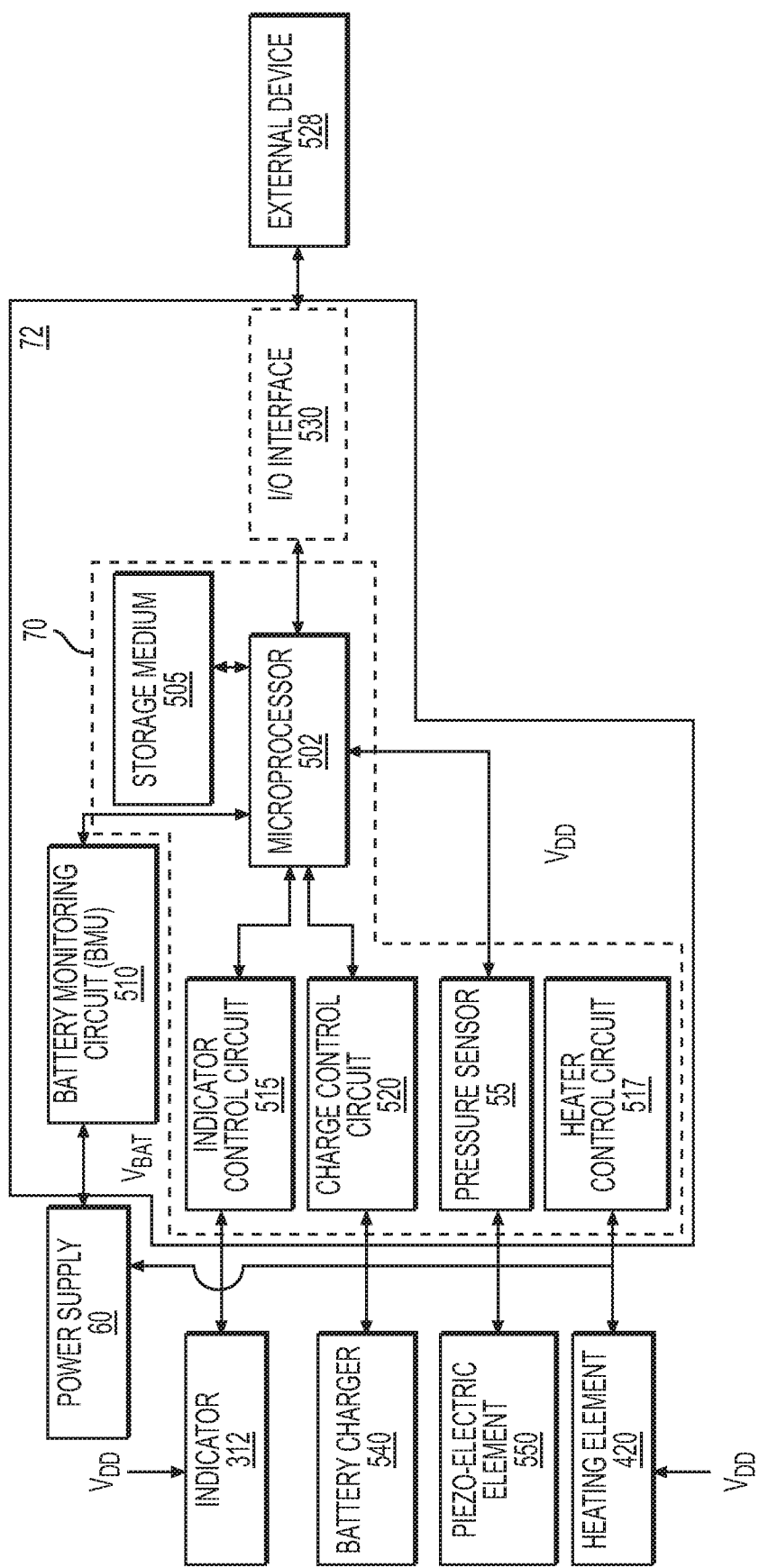
FIG. 5 illustrates an example circuit diagram of an example embodiment of an electronic vaping device.
Figure 6:
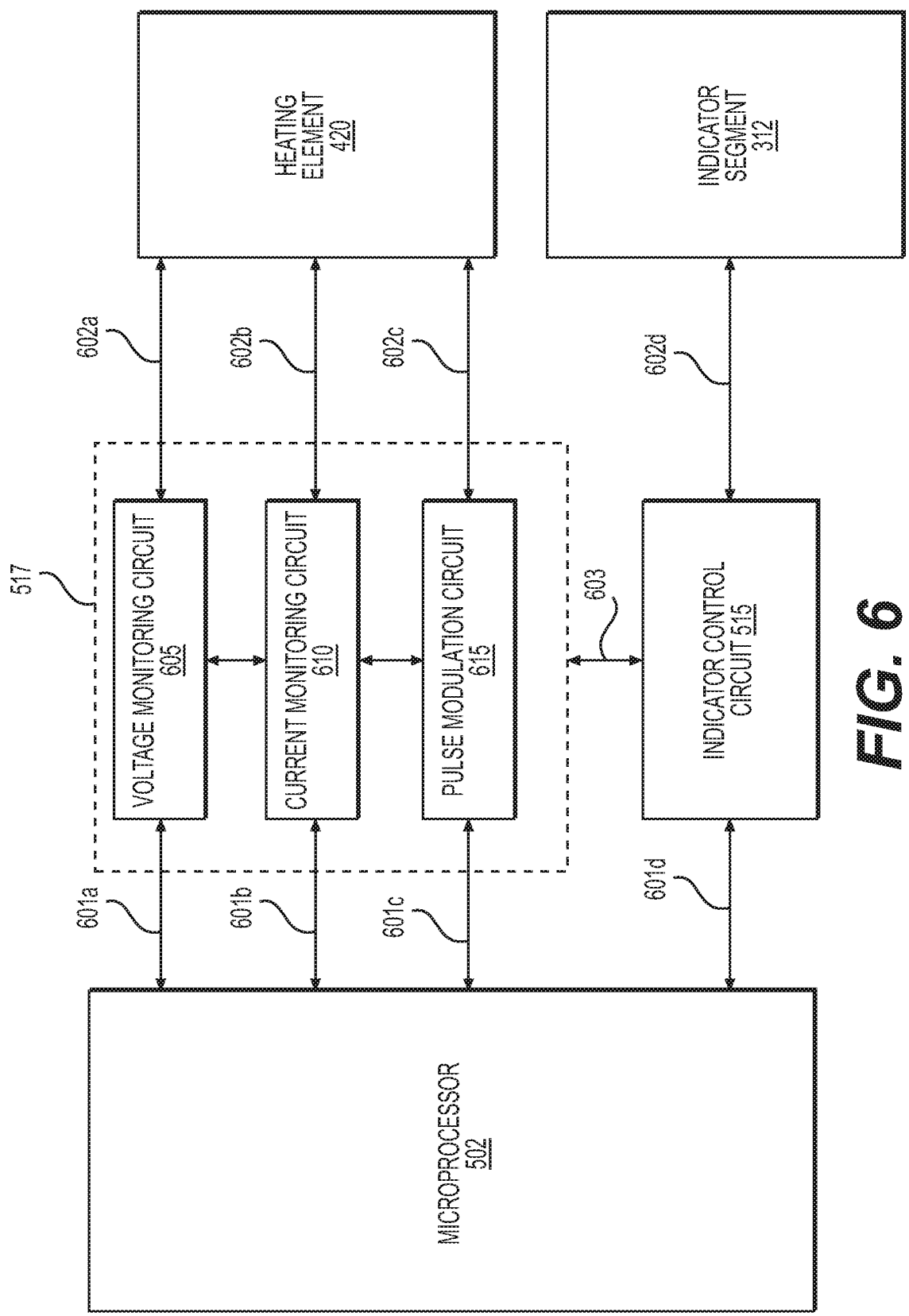
FIG. 6 illustrates an example information flow diagram embedded in a block diagram illustrating information flow within an electronic vaping device according to an example embodiment.

FIG. 5 illustrates a block diagram of the controller 70, according to an example embodiment. FIG. 6 is a schematic illustrating an embodiment of the indicator control circuit 515 and the heater control circuit 515 in more detail.

As shown in FIG. 5, the controller 70 includes a microprocessor 502, a computer-readable storage medium 505, an indicator control circuit 515, a heater control circuit 517, a charge control circuit 520, a battery management unit (BMU) 510 and a pressure sensor 55 on circuit board 72. In one example embodiment, the various components of the controller 70 and the microprocessor 502 communicate using an Inter-Integrated Circuit (I²C) interface. In at least some example embodiments, the circuit board 72 further includes an external device input/output interface 530 for an external device 528. The I/O interface 530 may be a Bluetooth interface, for example.

The controller 70 controls features of the power section 30, as well as the entire e-vaping device 10, such as controlling the heating element 420, interfacing with an external charger 540 and monitoring the pressure within the e-vaping device 10 to determine whether an adult vesper has applied a negative pressure. The controller 70 may be hardware, firmware, hardware executing software or any combination thereof. For example, the controller 70 may be one or more Central Processing Units (CPUs), digital signal processors (DSPs), one or more circuits, application-specific-integrated-circuits (ASICs), field programmable gate arrays (FPGAs), and/or computers or the like configured as special purpose machines to perform the functions of the controller 70.

For instance, if the controller 70 is a processor executing software, the controller 70 executes instructions stored in the computer readable storage medium 505 to configure the controller 70 as a special purpose machine.

As disclosed herein, the term "computer readable storage medium" or "non-transitory computer readable storage medium" may represent one or more devices for storing data, including read only memory (ROM), random access memory (RAM), magnetic RAM, core memory, magnetic disk storage mediums, optical storage mediums, flash memory devices and/or other tangible machine readable mediums for storing information. The term "computer-readable storage medium" may include, but is not limited to, portable or fixed storage devices, optical storage devices, and various other mediums capable of storing, containing or carrying instruction(s) and/or data.

As shown in FIG. 5, the power supply 60 supplies a voltage $V_{BAT}$ to internal circuitry, e.g., the microprocessor 502, indicator control circuit 515, the heater control circuit 517, the pressure sensor 55, and the charge control circuit 520. Based on the voltage $V_{BAT}$ and data from the microprocessor 502 to the indicator control circuit 515, the indicator 312 produces a light or series of lights indicates an amount of pre-vapor formulation in the reservoir.

The indicator control circuit 515 and the charge control circuit 520 are controlled by the microprocessor 502 and transmit/receive data to/from the microprocessor 502.

The heater control circuit 517 is configured to control a voltage supplied to the heating element 420 based on a pulse-width modulation signal and an enable signal from the microprocessor 502. For example, when the microprocessor 502 detects that the cartridge 20 and power section 30 are connected, the heater control circuit 517 is configured to monitor a voltage across the heating element 420 and a current through the heating element 420. The heater control circuit 517 is configured to feedback the monitored voltage and current through the heating element 420 to the microprocessor 502. The microprocessor 502 is then configured to adjust the pulse-width modulation signal based on the feedback from the heater control circuit 517. This operation will be described in more detail below with respect to FIGS. 6 and 7.

The BMU 510 monitors a voltage $V_{BAT}$ generated by the power supply 60. If the voltage $V_{BAT}$ is within a set range (e.g., between 2.5V and 4.3V), the BMU 510 supplies the voltage $V_{BAT}$ to the microprocessor 502. If the voltage $V_{BAT}$ is not within the set range, the BMU 510 prevents power being supplied to the microprocessor 502.

The microprocessor 502 includes a voltage regulator to convert the voltage $V_{BAT}$ to a supply voltage $V_{DD}$. The microprocessor 502 supplies the voltage $V_{DD}$ to the pressure sensor 55, the indicator 312 and the heater 420.

The pressure sensor 55 may be a microelectromechanical system (MEMS) sensor. The microprocessor 502 uses the MEMS pressure sensor 55 including a piezo-electric element 550 to determine whether an adult vaper has applied a negative pressure to the e-vaping device 10. When the microprocessor 502 detects an adult vaper applying a negative pressure, the microprocessor 502 controls the heater control circuit 517 to begin a heating process for the heating element 420 to create a vapor by vaporizing the pre-vapor formulation. The pressure sensor 55 is generally set on an end of the device and put into a gasket that seals one side of the sensor from another side of the sensor. The MEMS pressure sensor 55 may be an MS5637-02BA03 Low. Voltage Barometric Pressure Sensor, for example. An airflow sensor may be used in place of the MEMS sensor or in addition to the MEMS sensor.

As shown in FIG. 6, the heater control circuit includes a voltage monitoring circuit 605 is coupled to the microprocessor 502 via interface 601a and the voltage monitoring circuit 605 is coupled to the heating element 420 via interface 602a. The current monitoring circuit 610 is coupled to the microprocessor 502 via interface 601b and the current monitoring circuit 610 is coupled to the heating element 420 via interface 602b. A pulse modulation circuit 615 is coupled to the microprocessor 502 via interface 601c, the pulse modulation circuit 615 is coupled to the heating element 420 via interface 602c. The indicator control circuit 515 is coupled to the microprocessor 502 via interface 601d, and the indicator control circuit 515 is coupled to at least one of a possible plurality of indicator segments 312 via interface 602d. The indicator control circuit 515 is coupled to the heater control circuit 517 via interface 603. The indicator control circuit 515 is coupled to the discrete segment(s). The interfaces 601a, 601b and 601c may be one or more pins.

The heater control circuit 517 includes the voltage monitoring circuit 605 and a current monitoring circuit 610. The heater control circuit 517 also includes a pulse modulation circuit 615. It will be understood that the heater control circuit 517 may include other circuits as well, but those other circuits have been omitted for the sake of brevity. The voltage monitoring circuit 605 may be a voltage detector. The current monitoring circuit 610 may be a current detector.

Figure 7:
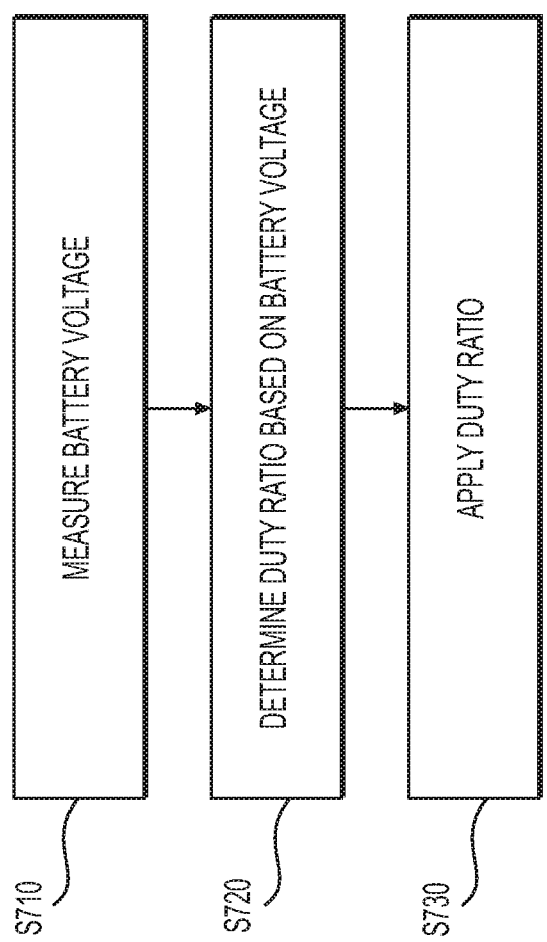
FIG. 7 is a flow chart illustrating an indicator initialization process according to an example embodiment.

FIG. 7 illustrates an initialization process. An initialization process may be triggered in at least one of a plurality of different ways. For example, in some example embodiments, an initialization process may be triggered when a cartridge is connected to a power section. In other example embodiments, an initialization process may be triggered when an adult vesper applies a negative pressure to the cartridge. In further example embodiments, an initialization process may be triggered when the e-vaping device is moved from a resting position. For example purposes the example embodiment shown in FIG. 7 will be described with respect to the diagrams shown in FIGS. 5 and 6.

The initialization process results in an applied duty cycle for power supply to the heating element 420. For example, the microprocessor 502 obtains a desired power from the storage medium 505. The desired power may be a design parameter, empirically determined, and pre-stored in the storage medium 505 by a manufacturer.

Referring to FIG. 7, at step S710, the controller 70, via the battery management unit 710, which may be an analog-digital converter, measures a voltage of the power supply 60. At step S720, the controller 70 determines a duty cycle based on the measured voltage. At step S730, the controller 70 applies the duty cycle to the heating element 720. Determination and application of the duty cycle will be explained in more detail below with respect to FIG. 8. Although example embodiments are described with respect to the process shown in FIG. 7, any known initialization process may be used. U.S. patent application Ser. No. 15/191,778, the entirety of which is herein incorporated by reference, is an example of another initialization process that may be used with example embodiments.

Figure 8:
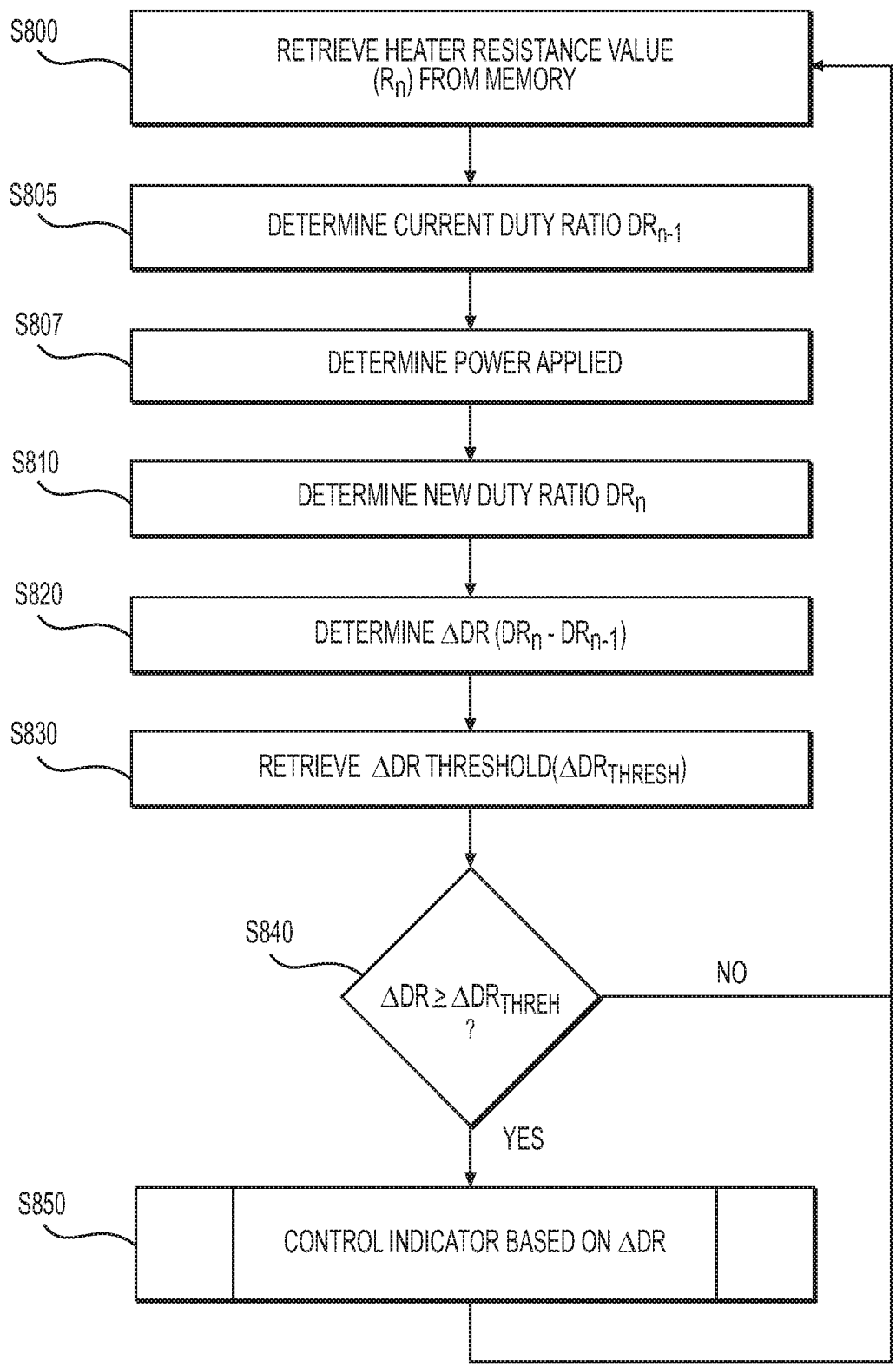
FIG. 8 is a flow chart illustrating an indicator control process according to an example embodiment.

FIG. 8 illustrates a flow chart of an indicator control process according to an example embodiment.

Referring to FIG. 8, in step S800, the controller 70 retrieves a resistance value for the heating element 420 from the storage medium 505. The resistance value may be stored in the storage medium 505 when the e-vaping device is manufactured. At step S805, the controller 70 determines a current duty cycle based on the battery voltage. For example, the microprocessor 502 obtains a desired power from the storage medium 505. The desired power may be a design parameter, empirically determined, and pre-stored in the storage medium 505 by a manufacturer. In one example embodiment, the desired power may be 3.9 W. The microprocessor 502 also obtains a start resistance $R_{start}$ from the storage medium 505. The start resistance $R_{start}$ is an assumed resistance for the heater 420. The start resistance $R_{start}$ may be a design parameter, empirically determined, and pre-stored in the storage medium 505 by a manufacturer. In one example, the start resistance may be about 3.5 Ohms. The microprocessor 502 uses the measured battery voltage, the desired power and the start resistance to determine the duty cycle (DR) (or duty ratio) according to the following equation:

$$DR_{n-1} = \frac{(\text{Desired Power})(R_{Start})}{V_{BAT}^2} \quad (1)$$

where $DR_{n-1}$ is the duty cycle determined using equation (1) and $V_{BAT}$ is the measured battery voltage.

For example, at step S807, the controller 70 determines a power applied to the heating element 420 based on the current duty cycle $DR_{n-1}$. The microprocessor 502 may calculate the applied power ($\text{Power}_{Applied}$) using the following equation:

$$\text{Power}_{Applied} = \frac{V_{Sample} * I_{Sample}}{DR_{n-1}} \quad (2)$$

where $V_{Sample}$ is the measured voltage and $I_{Sample}$ is the measured current across the heating element 420.

At step S810, the controller 70 determines a new duty cycle $DR_n$ for use in applying power to the heating element 420. For example, the microprocessor 502 determines the new duty cycle according to the following equation:

$$DR_n = \frac{(\text{Desired Power}) * DR_{n-1}}{\text{Power}_{Applied}}. \quad (3)$$

Additional methods of determining a duty ratio are disclosed in U.S. patent application Ser. No. 15/191,778, which is incorporated herein by reference in its entirety.

Referring back to FIG. 6 for example, the voltage monitoring circuit 605 samples a filtered (e.g., average) voltage across the heating element 420 and the current monitoring circuit 610 samples a filtered (e.g., average) current through the heating element 420. The controller 70 receives the voltage measurement from the voltage measuring circuit 605 and the current measurement from the current measuring circuit 610. As will be appreciated, these and any other measurements received by the controller 70 may undergo analog-to-digital conversation. The controller 70 may store the measured voltage and the measured current in the storage medium 505.

The controller 70 stores the new duty cycle in the storage medium 505. The controller 70 continues the application of power to the heating element 420, but does so according to the new duty cycle. For example, the microprocessor 502 controls the power modulation circuit 615 to provide a pulse width modulated power signal to the heating element 420 according to the new duty cycle.

At step S820, the controller 70 determines a difference between the current duty cycle and the new duty cycle to retrieve a duty cycle difference (ΔDR). Then at step S830, the controller retrieves a duty cycle threshold $\Delta DR_{thresh}$ from the medium 505. The controller 70 compares $\Delta DR$ with the $\Delta DR_{thresh}$ at step S840. For example, if the controller 70 determines that $\Delta DR$ is less than $\Delta DR_{thresh}$, the controller 70 will return to step S800. On the other hand, if the controller 70 determines that $\Delta DR$ is greater than $\Delta DR_{thresh}$, the controller 70, at step S850 controls the indicator based on the $\Delta DR$. Step S850 will be discussed in more detail below.

As will be appreciated, in a next iteration, the duty cycle $DR_{n-1}$ equals the new duty cycle $DR_n$ from the previous iteration. However, if the application of negative pressure has ended, then the process ends.

In one example embodiment, a cycle time for the initiation process and a cycle time for one iteration of the closed loop power control process may be set equal. However, example embodiments are not limited to these processes having equal starting time. In one example embodiment, the cycle time may be about 60-80 ms. However, the example embodiments are not limited to these values.

As will be appreciated, the method of FIGS. 7-8 is repeated during each application of negative pressure. In one example embodiment, after a first application of negative pressure, a start resistance may be determined based on the last measured voltage across the heating element 420 divided by the last measured current applied to the heating element 420.

In an alternative embodiment, the process of FIGS. 7-8 may be based on a desired voltage for application to the heating element 420 instead of a desired power. The desired age may be a design parameter, empirically determined, and pre-stored in the storage medium 505 by a manufacturer. For example, instead of determining the new duty cycle according to equation (3), the new duty cycle may be determined according to equation (4) below:

$$DR_n = \frac{(\text{Desired Voltage}) * DR_{n-1}}{V_{sample}}. \quad (4)$$

In yet another alternative embodiment, the process of FIGS. 7-8 may be based on a desired current for application to the heating element 420 instead of a desired power. The desired current may be a design parameter, empirically determined, and pre-stored in the storage medium 505 by a manufacturer. For example, instead of determining the new duty cycle according to equation (3), the new duty cycle may be determined according to equation (5) below:

$$DR_n = \frac{(\text{Desired Voltage}) * DR_{n-1}}{I_{sample}}. \quad (5)$$

Figure 9:
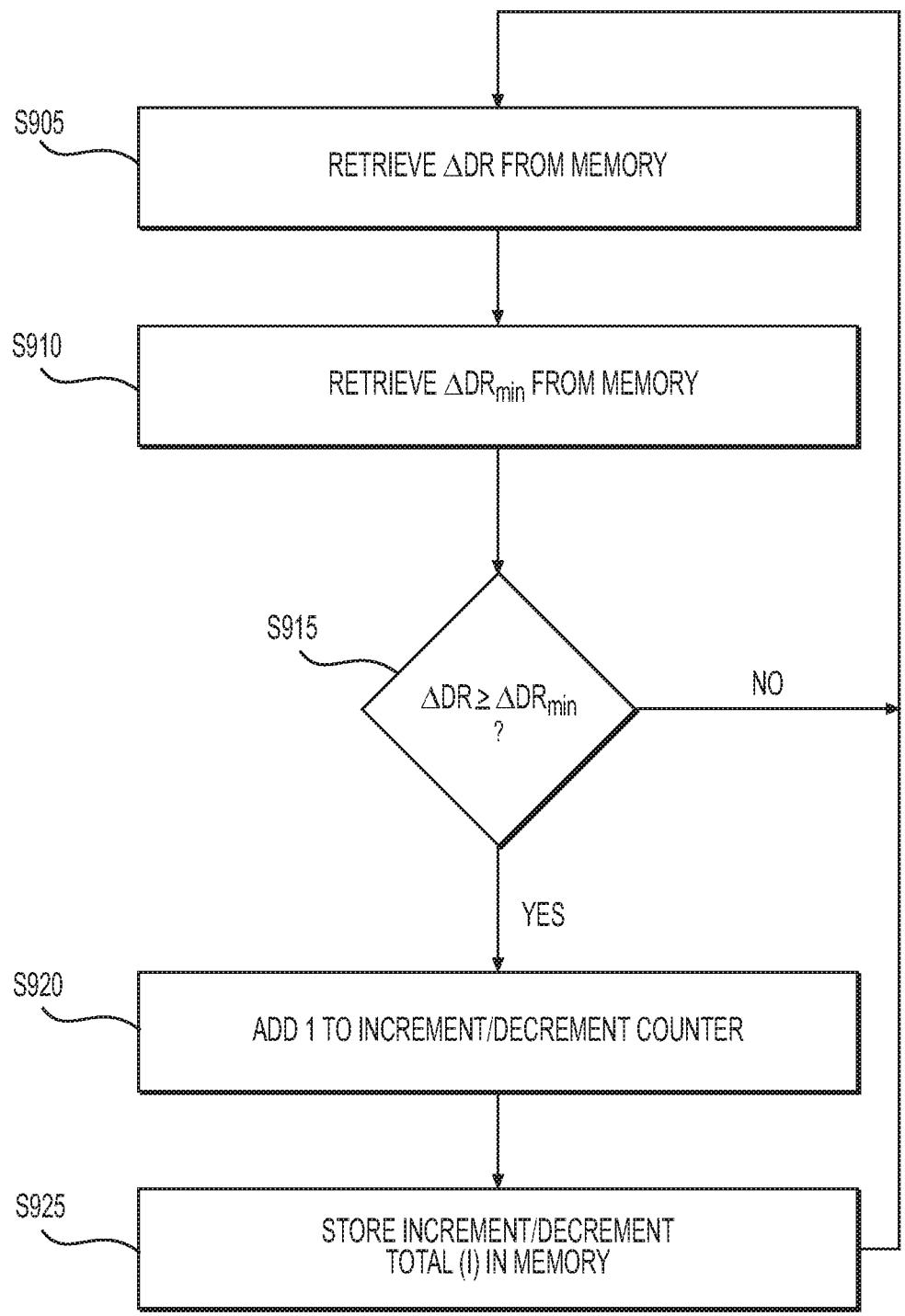
FIG. 9 is a flow chart illustrating another indicator control process according to an example embodiment.

FIG. 9 illustrates a flowchart illustrating the indicator control process 850 of FIG. 8. At step S905, the $\Delta DR$ determined above in step S820 is either used directly upon its determination or it is retrieved from the storage medium 505. At step S910, a $\Delta DR_{min}$ is retrieved from the storage medium 505. The $\Delta DR_{min}$, for example is a benchmark value upon which a change in the indicator is executed. Thus, at step S915, $\Delta DR$ is compared with $\Delta DR_{min}$ to determine whether the benchmark is met.

If $\Delta DR$ is less than $\Delta DR_{min}$, the process returns to the start. On the other hand, if $\Delta DR$ is greater than $\Delta DR_{min}$, the controller 70 changes the power to the discrete segments by a single increment/decrement unit. A unit, for example, may be equivalent to providing power to a new discrete segment 312a of the indicator 312. Any relationship between the duty cycle and the increment/decrement unit may be determined by a manufacturer. For example, a duty cycle of twenty-five percent may cause power to be directed toward all of the discrete segments 312a. Further, a duty cycle of seventy-five percent may cause power to be directed toward one discrete segment (or no discrete segments). Further still, a duty cycle of fifty percent may cause the power to be directed toward half of the discrete segments.

In view of the process disclosed herein, it is understood that the controller 70 would decrease the power to the discrete segment upon determining that $\Delta DR$ is greater than $\Delta DR_{min}$.

At step S920, an increment/decrement counter is increased by one when the power is incremented. At step S925, an increment/decrement total, e.g., the total of all increments or decrements occurring since a cartridge is stored in the storage medium 505. The increment/decrement total counter is retrieved later to determine, after a vaping session ends and upon initiating a new vaping session, how many discrete segments the controller should provide power for the new vaping session. For example, if there are ten discrete segments on the cartridge 20, and the increment/decrement counter has a value of five, then five of the discrete segments can be powered.

Figure 10:
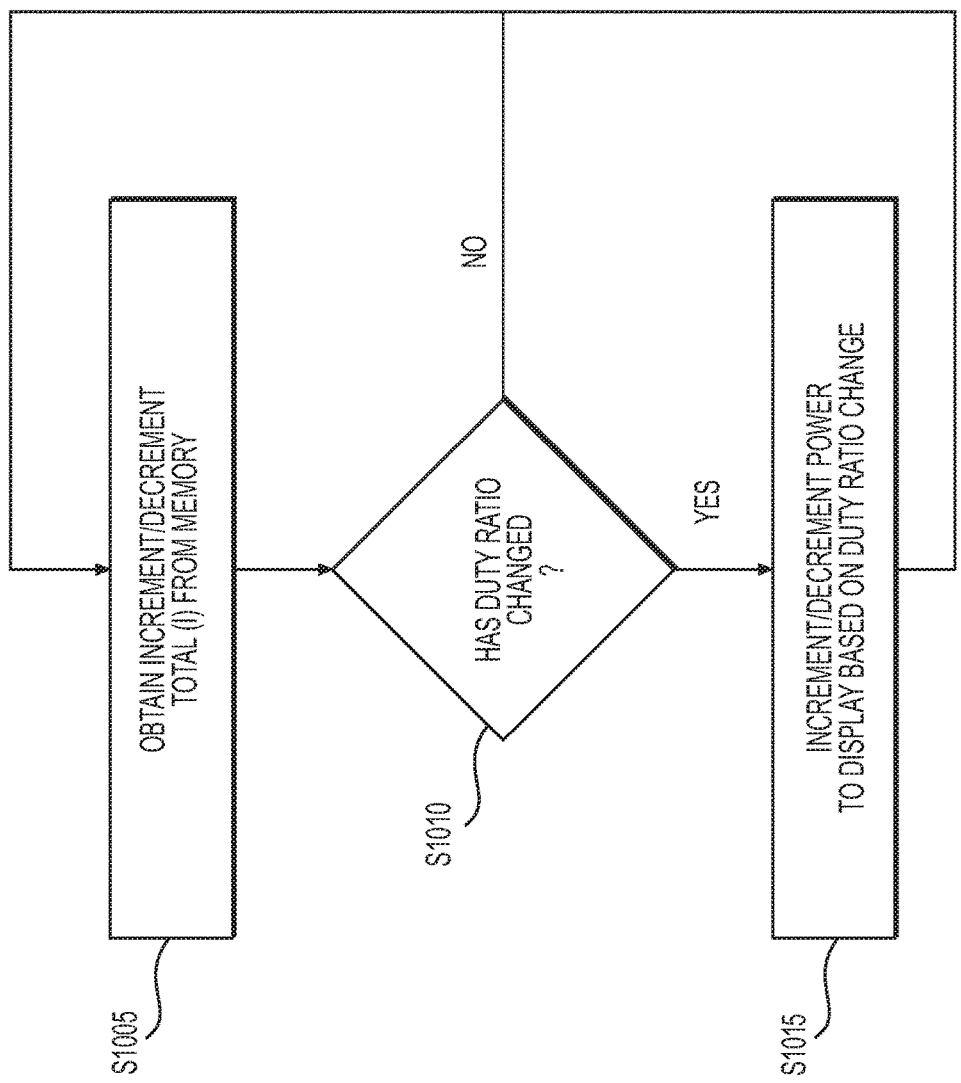
FIG. 10 is a flow chart illustrating yet another indicator control process according to an example embodiment.

A further example embodiment is illustrated in FIG. 10. FIG. 10 illustrates a process for updating an indicator of a cartridge having a static indicator, such as e-paper, after the indicator has been adjusted, power to the indicator section has been discontinued, and power to the discrete segment has been reestablished. At step S1005, the controller 70 obtains the increment/decrement total (I) from the storage medium 505. At step S1010, the controller 70 determines whether the duty cycle has changed. If not, the process returns to S1005 and repeats. On the other hand, if the duty cycle has changed, at step S1015, the controller 70 increases or decreases power to the indicator based on the new duty cycle as described above.

In some example embodiments, the controller 70 may apply a 100% duty cycle of power to the heating element 420 for a short period of time only a few milliseconds). This may occur when the multi-port insert 50 is attached or at a first application of negative pressure. The controller 70 measures the voltage and current across the heating element 420 and determines the resistance of the heating element 420. If the resistance is outside of a desired range, then the multi-port insert 50 is identified as invalid, and no further power will be supplied to the multi-port insert 50. The desired range may be a design parameter, empirically determined, and stored in the storage medium 505. For example the desired range may be about 2 to 5 Ohms. The controller 70 may be configured to ignore any duty cycles outside of a certain range. For example, duty cycles of one hundred percent and duty cycles of ten percent may be ignored.

Figure 11:
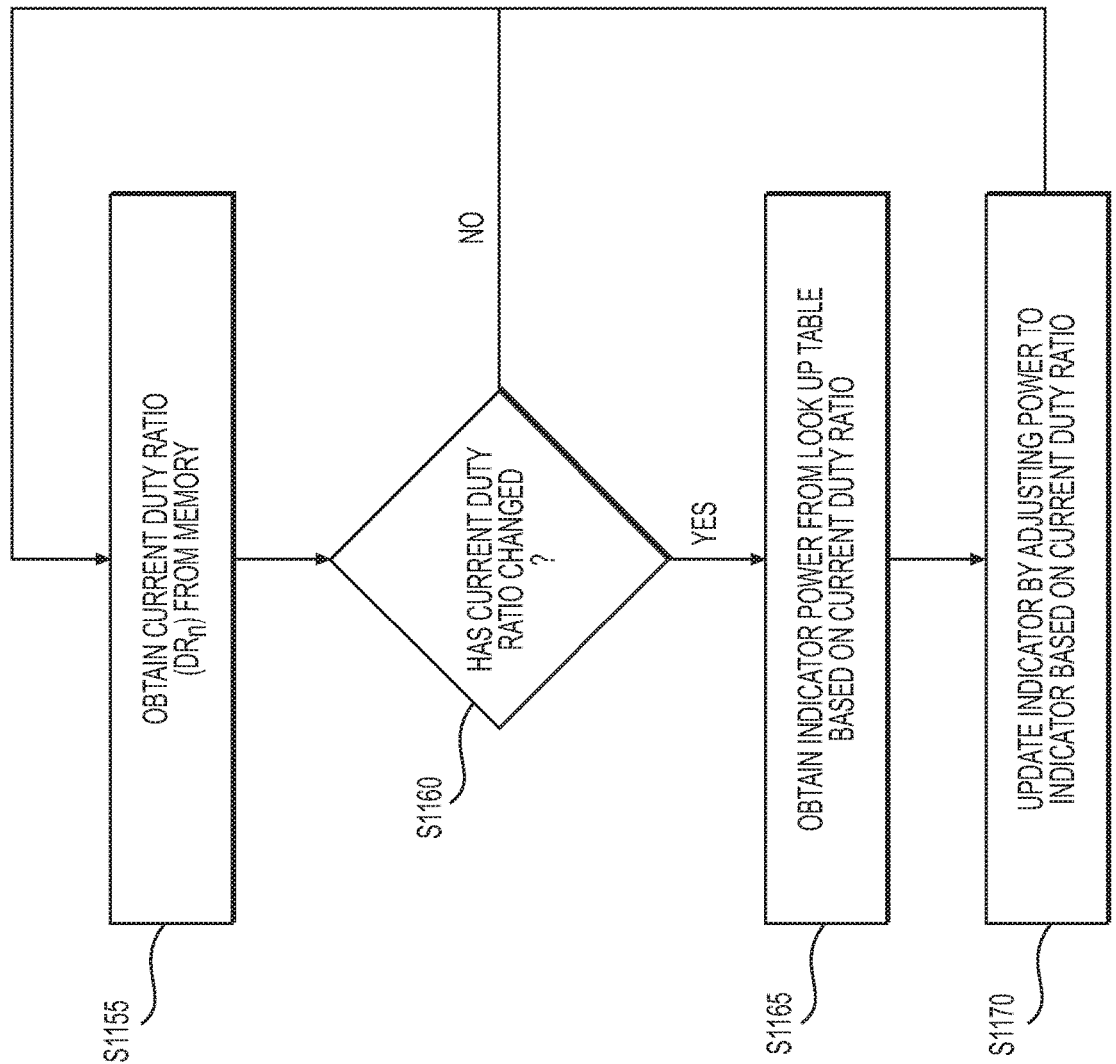
FIG. 11 illustrates a process for updating an indicator of a cartridge.

A further example embodiment is illustrated in FIG. 11. FIG. 11 illustrates a process 1150 for updating an indicator of a cartridge based on a relationship between the duty cycle and an amount of power to be applied to the indicator A look up table may be stored in the storage medium 505 (e.g., at the time of manufacturing). The look up table may contain a relationship matrix where an amount of power applied to the indicator is related to a particular duty cycle. The values in the relationship matrix may be determined empirically before the e-vaping device 10 is manufactured.

Alternatively, the relationship matrix may be uploaded to the storage medium 505 after manufacture.

As the duty cycle changes, the amount of power to the indicator changes as well. For example, as shown in FIG. 11, at step S1155, the microprocessor 502 obtains a current duty cycle from the storage medium 505. At step S1160, the microprocessor 502 determines whether the duty cycle has changed based on the process discussed above relating to FIGS. 8 and 9. If the microprocessor 502 determines that the duty cycle has not changed, then the process returns to step S1155. At step S1165, the microprocessor 502 obtains from a look-up table in the storage medium 505 a power to be applied to the indicator based on the current duty cycle. At step 1170, the microprocessor 502 updates the indicator by adjusting power to the indicator.

As noted above, different pre-vapor formulations may be included in e-vaping devices according to example embodiments. According to at least some example embodiments, the beginning resistance ($R_{START}$) may change depending on the type of pre-vapor formulation that is included in the e-vaping device. A pre-vapor formulation look-up table may be included in the e-vaping device. The pre-vapor formulation look-up table may include information specific to a particular type of pre-vapor formulation.

In some example embodiments, the storage medium 505 of the controller 70 within the power section 30 may include a look-up table having information on various different pre-vapor formulations. For example, a first type of pre-vapor formulation may have a resistance that differs from a resistance of a second type of pre-vapor formulation. Through, for example, RFID, an EPROM, a resistor, or the like, a cartridge 20 may be configured to communicate to the processor 502 what type of pre-vapor formulation is contained therein. The processor 502 may retrieve the resistance $R_{START}$ from the look-up table in the storage medium 505 for use in determining a fluid level as discussed herein.

In other example embodiments, the processor 502 may determine $R_{START}$ when pre-vapor formulation information is not included in the look-up table. For example, the cartridge 20 may include data that is indicative of the resistance of the particular pre-vapor formation within the cartridge 20. The processor 502 may be configured to retrieve e.g., directly) from the cartridge 20 data relating to the resistance of the particular pre-vapor formulation within the cartridge and determine the fluid level accordingly. In these other example embodiments, the data relating to the resistance of the particular pre-vapor formation may be stored in hardware such as an EPROM or embodied in a resistor having a particular value at the cartridge 20 to indicate to the processor 502 the resistance of the pre-vapor formulation within the cartridge 20.

For example, in some example embodiments, the processor 502 may retrieve a resistance value from the EPROM in the cartridge 20 and may use that retrieved resistance value, as discussed above, to determine a fluid level.

Alternatively, in other example embodiments, a cartridge 20 may include an identification resistor that has a resistance value that enables the processor 502 to determine a fluid level as discussed herein. For example, the processor 502 may apply a voltage to the identification resistor to determine the resistance value of the identification resistor and then, as disclosed herein, the processor 502 may determine a fluid level based on the determined resistance value.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

We claim:

1. A vaporizer assembly for an electronic vaping device, the vaporizer assembly comprising:
    a heating element;
    a pre-vapor formulation reservoir configured to contain a pre-vapor formulation;
    a pre-vapor formulation level indicator including a plurality of indicator segments; and
    at least one processor configured to
    determine a difference between a first duty cycle of power supplied to the heating element and a second duty cycle of power supplied to the heating element; and
    adjust the indicator based on the determined duty cycle difference.

2. The electronic vaping device as recited in claim 1, wherein the at least one processor is further configured to
    increase an amount of indicator segments that receive power in proportion to the determined duty cycle difference.

3. The electronic vaping device as recited in claim 2, wherein the at least one processor is further configured to
    decrease an amount of indicator segments that receive power in proportion to the determined duty cycle difference.

4. The electronic vaping device as recited in claim 3, wherein the at least one processor is further configured to
    increase the amount of indicator segments in proportion to the determined duty cycle.

5. The vaporizer assembly for the electronic vaping device as recited in claim 2, wherein the pre-vapor formulation level indicator includes an electronic paper film.

6. The vaporizer assembly for the electronic vaping device as recited in claim 5, wherein the processor is further configured to
    provide power to the indicator segments in an amount proportional to an amount of decrease in a pre-vapor formulation in the pre-vapor formulation reservoir.

7. The vaporizer assembly for the electronic vaping device as recited in claim 2, wherein the pre-vapor formulation level indicator is backlit.

8. The vaporizer assembly for the electronic vaping device as recited in claim 7, wherein the processor is further configured to
    direct power to indicator in an amount proportional to an amount of decrease in a pre-vapor formulation in the pre-vapor formulation reservoir.

9. The vaporizer assembly for the electronic vaping device as recited in claim 2, wherein the pre-vapor formulation level indicator is an organic light emitting diode (OLED).

10. The vaporizer assembly for the electronic vaping device as recited in claim 9, wherein the processor is further configured to
    direct power to the indicator in an amount proportional to an amount of decrease in a pre-vapor formulation in the pre-vapor formulation reservoir.

11. The vaporizer assembly for the electronic vaping device as recited in claim 1, wherein the processor is further configured to determine at least one of the first and second duty cycles based on a type of pre-vapor formulation within the pre-vapor formulation reservoir.

12. A vaporizer assembly for an electronic vaping device, the vaporizer assembly comprising:
a heating element;
a pre-vapor formulation reservoir configured to contain a pre-vapor formulation;
a pre-vapor formulation level indicator including an indicator; and
at least one processor configured to
determine a difference between a first duty cycle of power supplied to the heating element and a second duty cycle of power supplied to the heating element; and
adjust the indicator based on the determined duty cycle difference.

13. The electronic vaping device as recited in claim 12, wherein the indicator includes
a plurality of pre-vapor formulation level indicator segments.

14. The electronic vaping device as recited in claim 12, wherein the at least one processor is further configured to
decrease power to the indicator in proportion to the determined duty cycle.

15. The electronic vaping device as recited in claim 12, wherein the at least one processor is further configured to
increase power to the indicator in proportion to the determined duty cycle.

16. The electronic vaping device as recited in claim 15, wherein the at least one processor is further configured to
decrease power to the indicator in proportion to the determined duty cycle.

17. The vaporizer assembly for the electronic vaping device as recited in claim 12, wherein indicator includes an electronic paper film.

18. The vaporizer assembly for the electronic vaping device as recited in claim 17, wherein the processor is further configured to
provide power to the indicator in an amount proportional to an amount of decrease in a pre-vapor formulation in the pre-vapor formulation reservoir.

19. The vaporizer assembly for the electronic vaping device as recited in claim 12, wherein the pre-vapor formulation level indicator is backlit.

20. The vaporizer assembly for the electronic vaping device as recited in claim 19, wherein the processor is further configured to
provide power to the indicator in an amount proportional to an amount of decrease in a pre-vapor formulation in the pre-vapor formulation reservoir.

21. The vaporizer assembly for the electronic vaping device as recited in claim 12, wherein the pre-vapor formulation level indicator is an organic light emitting diode (OLED).

22. The vaporizer assembly for the electronic vaping device as recited in claim 21, wherein the processor is further configured to
provide power to the indicator in an amount proportional to an amount of decrease in a pre-vapor formulation in the pre-vapor formulation reservoir.

23. The vaporizer assembly for the electronic vaping device as recited in claim 12, wherein the processor is further configured to
determine at least one of the first and the second duty cycles based on a type of pre-vapor formulation within the pre-vapor formulation reservoir.

* * * * *